United States Patent [19]
Drent et al.

[11] Patent Number: 5,488,174
[45] Date of Patent: Jan. 30, 1996

[54] HYDROFORMYLATION PROCESS

[75] Inventors: Eit Drent; Dennis H. L. Pello; Jacoba C. L. J. Suykerbuyk, all of Amsterdam, Netherlands

[73] Assignee: Shell Oil Company, Houston, Tex.

[21] Appl. No.: 289,714

[22] Filed: Aug. 12, 1994

[30] Foreign Application Priority Data

Aug. 19, 1993 [EP] European Pat. Off. ............ 93202447

[51] Int. Cl.⁶ .................................................. C07C 45/50
[52] U.S. Cl. .................. 568/454; 568/426; 568/429; 568/451; 568/455
[58] Field of Search .................................. 568/454, 451, 568/426, 429, 451, 454, 455

[56] References Cited

FOREIGN PATENT DOCUMENTS

| | | |
|---|---|---|
| 220767 | 5/1987 | European Pat. Off. . |
| 495547 | 7/1992 | European Pat. Off. . |
| 529698 | 3/1993 | European Pat. Off. . |

OTHER PUBLICATIONS

PCT/EP 94/02762 Search Report Oct. 26, 1994.

*Primary Examiner*—Werren B. Lone

[57] ABSTRACT

Process for the hydroformylation of ethylenically unsaturated compounds, by reaction with carbon monoxide and hydrogen in the presence of a catalyst based on a metal of the platinum group, a source of anions and a bidentate ligand of the formula $R^1R^2M^1RM^2R^3R^4$ wherein $M^1$ and $M^2$ are phosphorus, arsenic or antimony, R is a bivalent organic bridging group with 1 to 4 atoms in the bridge, $R^1$ and $R^2$ together represent a bivalent cyclic group and $R^3$ and $R^4$ independently represent an optionally substituted hydrocarbyl group or together have the same meaning as $R^1$ and $R^2$.

24 Claims, No Drawings

HYDROFORMYLATION PROCESS

FIELD OF THE INVENTION

The invention relates to a process for the hydroformylation of ethylenically unsaturated compounds by reaction thereof with carbon monoxide and hydrogen in the presence of a catalyst.

BACKGROUND OF THE INVENTION

The hydroformylation of ethylenically unsaturated compounds to form aldehydes and/or alcohols, is of considerable industrial importance. The process has been in commercial operation for decades and over the years much development work has been done to optimize the reaction conditions, the catalyst system and the equipment. Although significant progress as regards higher yield and selectivity to the desired reaction products has been made, it is felt that in some aspects further improvement of the process is still needed.

Conventional modes of operation were initially based on the use of a cobalt carbonyl catalyst. The activity of this catalyst is relatively low and moreover, when using internal olefins as starting material, a mixture of hydroformylation products is formed containing substantial amounts of branched compounds. For many applications, the presence of these branched compounds is undesirable. Moreover, in view of biological degradability, it is also considered advantageous to produce mixtures exhibiting high linear/branching ratios.

The formation of branched products can be suppressed by using a cobalt-phosphine complex as catalyst. However, at the relatively high reaction temperatures required for an adequate activity of this catalyst system, substantial amounts of saturated hydrocarbons are formed in addition to the desired hydroformylation products.

It has been proposed to use a rhodium-based catalyst for hydroformylation reactions. A limitation of this catalyst consists in that with internal olefins as the starting material, branched products are formed. In general, with a rhodium catalyst, the obtained hydroformylation product predominantly consists of aldehydes. For some uses, e.g. for applications in the detergent industry, alcohols are a preferred starting material. Attempts have therefore been made to enhance the formation of alcohols, rather than that of aldehydes e.g. by increasing the hydrogen/carbon monoxide ratio, but these modes of operation invariably result in the formation of substantial amounts of saturated hydrocarbons.

It would hence be attractive if reaction conditions could be selected and a catalyst could be found such that the production of these saturated compounds is minimized.

In EP 220767, a hydroformylation process is described wherein an alkenically unsaturated compound having at least 5 carbon atoms per molecule is contacted with carbon monoxide and hydrogen in the presence of an aprotic solvent and a catalyst, based on palladium, platinum or a compound of one of these metals, an anion of a carboxylic acid with a pKa of less than 2 and a bidentate of the formula $Q^1Q^2MQMQ^3Q^4$ wherein M represents phosphorus, arsenic or antimony, Q represents a divalent organic bridging group having at least three carbon atoms in the bridge and $Q^1 \ldots Q^4$ are similar or dissimilar optionally substituted hydrocarbyl groups.

From the experimental results revealed in the examples, it can be seen that under the selected reaction conditions, the conversion is about 65%, the amount of linear compounds in the product mixture is 67% and that, although predominantly aldehydes are obtained, some formation of paraffins also takes place.

EP 495547 relates to a variety of carbonylation reactions, e.g. for the preparation of ketones, esters, aldehydes and alcohols. The hydroformylation of ethylenically unsaturated compounds is also encompassed and illustrated by a number of working examples. According to one of these examples, an alpha-olefin (1-octene) may be hydroformylated at 90° C., using a catalyst, comprising palladium, 1,3-bis(diisopropylphosphino)propane and a sulfonic acid to form aldehydes (and some alcohols) with a linearity of about 85%, the conversion being about 67%. For the hydroformylation of internal olefins, this catalyst is significantly less active.

It has now been found that by selecting a catalyst based on a metal of the platinum group and on a bidentate ligand comprising at least one bivalent cyclic moiety, improved hydroformylation results are achieved as regards, inter alia, conversion rate, linearity of product and suppression of paraffin make.

SUMMARY OF THE INVENTION

The invention therefore relates to a process for the hydroformylation of ethylenically unsaturated compounds by reaction thereof with carbon monoxide and hydrogen in the presence of a catalyst system comprising:

a) a source of a metal of the platinum group;

b) a source of anions; and c) a source of bidentate ligands of the formula $$R^1R^2M^1RM^2R^3R^4 \qquad (I)$$

wherein $M^1$ and $M^2$ independently represent a phosphorus, arsenic or antimony atom, R represents a bivalent organic bridging group containing from 1 to 4 atoms in the bridge, $R^1$ and $R^2$ together represent a bivalent substituted or non-substituted cyclic group wherein the two free valencies are linked to $M^1$ and $R^3$ and $R^4$ either independently represent a substituted or non-substituted hydrocarbyl group, or together have the same meaning as $R^1$ and $R^2$.

DESCRIPTION OF THE PREFERRED EMBODIMENTS

In the present specification, the metals of the platinum group are defined as the metals with the atomic numbers 28, 46 and 78, i.e. nickel, palladium and platinum. Of these, palladium and platinum are preferred.

Examples of suitable metal sources are platinum or palladium compounds such as salts of palladium with nitric acid, sulfuric acid or sulfonic acids, salts of platinum or palladium with carboxylic acids with up to 12 carbon atoms, palladium- or platinum complexes, e.g. with carbon monoxide or acetylacetonate, or palladium combined with a solid material such as an ion exchanger or carbon. Palladium (II)-acetate and platinum (II) acetylacetonate are examples of preferred metal sources.

As anion source, any compound generating these anions may be used. Suitably, acids, or salts thereof, are used as sources of anions, such as, for example, any of the acids mentioned above, which may also participate in the salts of the metals of the platinum group.

In the catalyst systems of the invention, strong acids are preferably used as anion source, i.e. acids having a pKa value of less than 2, measured in aqueous solution at 18° C.

The anions derived from these acids are non-coordinating or weakly coordinating with the metals of the platinum group.

Typical examples of suitable anions are anions of phosphoric acid, sulfuric acid, sulfonic acids and halogenated carboxylic acids such as trifluoroacetic acid.

Sulfonic acids such as, for example, methanesulfonic acid, trifluoromethanesulfonic acid, tert butylsulfonic acid and p-toluenesulfonic acid are particularly preferred.

Also, complex anions are suitable, such as the anions generated by a combination of a Lewis acid such as $BF_3$, $AlCl_3$, $SnF_2$, $Sn(CF_3SO_3)_2$, $SnCl_2$ or $GeCl_2$, with a protic acid, such as a sulfonic acid, e.g. $CF_3SO_3H$ or $CH_3SO_3H$ or a hydrohalogenic acid such as HF of HCl, or a combination of a Lewis acid with an alcohol.

Examples of suitable anion-generating combinations are $H(BF_4)$, $H(SnCl_3)$, $H[SnCl_2.CF_3SO_3]$ and $H(PF_6)$.

In bidentate ligands of formula (I) (component c) of the catalyst system) $M^1$ and $M^2$ are preferably the same and, more preferably, are both phosphorus atoms, in which case the ligands are bisphosphines.

The organic bridging group, represented by R is preferably a group comprising two carbon atoms in the bridge. It has been observed that the reaction rate is usually considerably enhanced if, instead of a catalyst based on a three membered bridging group, for instance a trimethylene group, a catalyst is used based on a two membered bridging group, such as an ethylene group.

This is surprising, because in earlier hydroformylation processes, such as the ones disclosed in EP 220767 and EP 495547, bidentate ligands are used whereby the presence of a bridging group containing 3 or more carbon atoms is preferred, or, as in EP 220767, even required.

In general, the bivalent cyclic group, represented by $R^1$ together with $R^2$ comprises at least 5 ring atoms Preferably, the said bivalent group is a cycloalkylene group comprising from 6 to 9 ring atoms, more preferably a group having 8 ring atoms. As a rule, all ring atoms are carbon atoms, but bivalent cyclic groups containing one or two heteroatoms in the ring such as oxygen- or nitrogen atoms, are not precluded. Examples of suitable bivalent cyclic groups are 1,2-cyclooctylene, 1,3-cyclooctylene, 1,4-cyclooctylene, 1,5-cyclooctylene, 1,4-cycloheptylene, 1,3-cycloheptylene and 1,4-cyclohexylene groups.

If desired, cyclic groups containing one or more substituents may be used, such as methyl- or ethyl-substituted cyclic groups.

Preferred bivalent cyclic groups are a 1,5-cyclooctylene group, and a dimethyl-1,5-cyclooctylene group.

Mixtures of ligands comprising different bivalent cyclic groups may be used as well, e.g. mixtures of ligands with 1,4-cyclooctylene and ligands with 1,5-cyclooctylene groups.

In the ligands of formula (I), $R^3$ and $R^4$ may independently represent various non-cyclic or cyclic groups, optionally substituted with substituents such as alkoxy groups with 1 to 4 carbon atoms, halogen atoms or ($C_1$ to $C_4$ alkyl)amino groups.

Examples of suitable groups include alkyl groups such as ethyl, isopropyl, secondary butyl and tertiary butyl groups, cycloalkyl groups such as cyclopentyl and cyclohexyl groups, aryl groups such as phenyl and toluyl groups and bivalent groups such as a hexamethylene group. However, preferably $R^3$ together with $R^4$ represents a bivalent cyclic group, in particular the same group as the group represented by $R^1$ together with $R^2$ in which case the two free valencies of the bivalent cyclic group are, of course, linked to $M^2$ instead of $M^1$. Thus, a preferred ligand is bis(1,4-cyclooctylenephosphino) ethane.

For the preparation of the bidentate ligands, reference is made to known techniques, for example the method disclosed in UK 1127965.

The quantity in which the catalyst system is used, is not critical and may vary within wide limits. Usually, amounts in the range of about $10^{-8}$ to about $10^{-1}$, preferably in the range of about $10^{-7}$ to about $10^{-2}$ gram atom of platinum group metal per molecule of ethylenically unsaturated compound are used. The amounts of the participants in the catalyst system are conveniently selected such that per gram atom of platinum group metal, from about 0.5 to about 10, preferably from about 1 to about 6 moles of bidentate ligand are used, from about 0.5 to about 15, preferably from about 1 to about 8 moles of anion source or a complex anion source.

The ethylenically unsaturated compound, used as starting material, is preferably an olefin having from 2 to about 24 carbon atoms per molecule, or a mixture thereof. They may comprise one or more double bonds per molecule. Preferred are internal olefins having from about 4 to about 20 carbon atoms, or mixtures thereof. Such olefin mixtures are commercially readily available, for example, the olefin mixtures, obtained as products of a process for the oligomerization of ethylene, followed by a double bond isomerization and disproportionation reaction. In the process of the invention, these internal olefins, usually mixtures of linear internal olefins with about 6 to about 20 carbon atoms per molecule, or closer boiling fractions of such mixtures, can be hydroformylated at high rates and an almost complete conversion. Examples are mixtures of linear internal $C_6$ to $C_8$ olefins, and of linear internal $C_{10}$ to $C_{14}$ olefins.

Substituted olefins such as, for example unsaturated carboxylic acids, esters of such acids, or unsaturated esters of carboxylic acids, e.g. allylacetate, may also be used.

If desired, branched olefins such as propene trimer or isomeric butene dimers (Dimersol) may be used, but the hydroformylation product will then, of course, contain branched structures as well.

Carbon monoxide and hydrogen may be supplied in equimolar or non-equimolar ratios, e.g. in a ratio within the range of about 3:1 to about 1:3. Preferably, they are supplied in a substantially equimolar amount.

The hydroformylation can be suitably carried out at moderate reaction conditions. Temperatures in the range of 50° C. to 160° C. are recommended, with preferred temperatures being in the range of 70° C. to 130° C. Reaction pressures in the range of about 5 bar to about 100 bar are preferred, but lower or higher pressures may be selected, although they are not considered particularly advantageous.

Conveniently, the hydroformylation reaction may be carried out in the additional presence of a solvent.

Suitable solvents include ethers such as 2,5,8-trioxanonane (diglyme), diethylether and anisole, and alcohols, preferably having from 4 to 10 carbon atoms per molecule, such as butanol, octanol or ethylhexanol, or in general terms, the alcohol of the same composition as the alcohol produced in the present process.

In earlier hydroformylation processes, such as the process according to EP 495547, the use of an alcohol as solvent was often considered undesirable, since the used hydroformylation catalysts were also catalytically active in the formation of esters in a reaction involving an olefin, carbon monoxide and the solvent alcohol. However, the catalyst systems of the present invention in view of their high selectivity towards the desired hydroformylation product, allow the use of alcohols as solvent.

The process of the invention is quite suitably used for the preparation of alcohols from internal olefins at high rate, in particular by using a catalyst system as defined above, based on palladium as platinum group metal.

Furthermore, the process is very useful for the preparation of aldehydes having a high linearity, in particular by using a catalyst system as defined above, based on platinum as platinum group metal.

The invention will be illustrated by the non-limiting examples, as described hereinafter. The abbreviations, used in the Tables have the following meaning:

BCPE=1,2-bis(1,4-cylooctylenephosphino)ethane
BCPP=1,3-bis(1,4-cyclooctylenephosphino)propane
BBPE=1,2-bis(sec.butylphosphino)ethane
BBPP=1,3-bis(sec.butylphosphino)propane
BDPE=1,2-bis(2,6-dimethyl-1,4-cyclooctylenephosphino)ethane
BCPI=1,2-bis(1,4-cyclooctylenephosphino)propane
MSA=methanesulfonic acid
TFSA=trifluoromethanesulfonic acid
t.BSA=tert. butylsulfonic acid
EH=2-ethylhexanol
HBF$_4$=fluoroboric acid

EXAMPLES I–III

The experiments were carried out in a 250 milliliter (mL) magnetically stirred autoclave. The autoclave was charged with 20 mL of 1-octene, 20 mL 2,5,8-trioxanonane(diglyme), 0.25 millimoles (mmol) of palladium (II).acetate, 0.6 mmol of bisphosphine ligand and 1 mmol of methanesulfonic acid. After being flushed, the autoclave was pressurized with carbon monoxide and hydrogen to a partial pressure of 30 bar of each. Subsequently, the reactor was sealed and the contents were heated to the pre-set temperature and maintained at that temperature until the reaction was substantially complete. After cooling, a sample was taken from the contents of the reactor and analyzed by gas-liquid-chromatography. Further details and the results of the analysis can be found in Table I.

The calculated conversion rate is expressed as moles of product per gram atom of platinum group metal per hour.

The amount of produced paraffins was less than 1%.

TABLE I

| Ex. No. | Ligand | Anion source type | mmol | Temp. °C. | Rate mol/gat/h | Product(s), Selectivity % | Linearity % |
|---|---|---|---|---|---|---|---|
| I | BCPE | MSA | 1 | 125 | 250 | C$_9$-alcohol 98 | 67 |
| II | BCPE | MSA | 1 | 100 | 200 | C$_9$-alcohol 98 | 64 |
| III | BCPP | MSA | 1 | 95 | 100 | C$_9$-aldehyde 98 | 64 |

EXAMPLES IV–IX AND COMPARATIVE EXAMPLES A AND B

The experiments were performed substantially according to the procedure as described for Examples I–III. The autoclave was charged with 30 mL of internal olefins with 14 carbon atoms, 50 mL of a solvent, 0.25 mmol of palladium (II) acetate, 0.6 mmol of bisphosphine ligand and a specified amount of an acid catalyst component. In Example IX, 20 mL of isomeric butene dimers (Dimersol) were used, instead of 30 mL of internal C$_{14}$-olefins.

Further details and the analytical results are provided in Table II.

The amount of produced paraffins was less than 1%.

By comparing the results of Examples IV and VI, it can be seen, that by using a ligand comprising a bridging moiety with two atoms in the bridge a higher conversion rate at a lower temperature is achieved whereby more linear hydroformylation products are formed, than by using a ligand comprising a 3-membered bridging element.

The effect of using different acid catalyst components can be seen by comparing the results of Examples VII and VIII.

The results of comparative example A show, that by using a ligand, outside the scope of the invention, even at a relatively high temperature, predominantly aldehydes are formed of poor linearity and at low rate.

In the experiment of Comparative example B, it is shown that the use of an alcohol as solvent results in the formation of a considerable amount of ester.

TABLE II

| Ex. No. | Ligand | Anion Source Type | mmol | Solvent | Temp °C. | Rate mol/gat/h | Product(s) Selectivity % | Linearity % |
|---|---|---|---|---|---|---|---|---|
| IV | BCPE | TFSA | 1 | EH | 88 | 100 | $C_{15}$-alcohol> 98 | 62 |
| V | BCPE | HBF | 1 | EH | 115 | 200 | $C_{15}$-alcohol> 98 | 70 |
| VI | BCPP | TFSA | 1 | 1-octanol | 120 | 30 | $C_{15}$-alcohol> 98 | 53 |
| VII | BCPE | TFSA | 1 | anisole | 90 | 200 | $C_{15}$-alcohol> 98 | 78 |
| VIII | BCPE | t.BSA | 0.5 | anisole | 88 | 100 | $C_{15}$-alcohol> 98 | 47 |
| A | BBPE | TFSA | 0.5 | diglyme | 125 | <10 | $C_{15}$-alcohols 15% $C_{15}$-alcohol 85% | 45 45 |
| B | BBPP | MSA | 0.5 | EH | 145 | 20 | $C_{15}$-alcohol 70% 2-ethylhexylester of $C_{15}$-alkanolc acid 30% | 50 |

TABLE II$^A$

| Ex No | Ligand | Anion Source Type | mmol | Solvent | Temp °C. | Rate mol/gat/h | Product(s) Selectivity % | Linearity % |
|---|---|---|---|---|---|---|---|---|
| IX | BCPE | MSA | 0.5 | EH | 110 | 95 after 20 h | $C_9$-Dimersol alcohols >98 | — |

EXAMPLES X–XVII

The experiments were performed substantially as described above for Examples I–III.

The autoclave was charged with 20 mL of 1-octene, 40 mL of diglyme, 0.25 mmol of platinum (II) acetylacetonate, 0.6 mmol of bisphosphine ligand and a specified amount of an acid catalyst component and/or other anion source.

Further details and results are provided in Table III.

Comparing the results of Examples XIV and XV with those of Example XIII shows that the addition of acid (acetic acid) results in an increase in rate of conversion.

TABLE III

| Ex No. | Ligand | Anion source type | mmol | Temp °C. | Rate mol/gat/h | Product(s) | Linearity % |
|---|---|---|---|---|---|---|---|
| X | BCPE | t.BSA | 1 | 137 | 50 | $C_9$-alcohol | 91 |
| XI | BCPE | TFSA | 1 | 128 | 100 | $C_9$-aldehyde $C_9$-alcohol | 88 |
| XII | BCPE | SnCl$_2$ | 1 | 125 | 70 | $C_9$-aldehyde | 98 |
| XIII | BCPE | TFSA SnCl$_2$ | 0.5 0.5 | 88 | 150 | $C_9$-aldehyde | 98 |
| XIV | BCPE | TFSA* SnCl$_2$ | 0.5 0.5 | 75 | 300 | $C_9$-aldehyde | 98 |
| XV | BCPE | TFSA* SnCl$_2$ | 0.5 0.5 | 90 | 500 | $C_9$-aldehyde | 98 |
| XVI | BDPE | TFSA SnCl$_2$ | 0.5 0.5 | 80 | 100 | $C_9$-aldehyde | 99.3 |
| XVII | BCPI | TFSA SnCl$_2$ | 0.5 0.5 | 80 | 150 | $C_9$-aldehyde | 98.6 |

*5 mL of acetic acid was added.

EXAMPLES XVIII–XX

The experiments were performed substantially as described in Examples X–XVII with the difference that 20 mL of propene was supplied, instead of 1-octene.

The selectivity to $C_4$-aldehydes was >98%.

Further details and results are provided in Table IV.

TABLE IV

| Ex No | Ligand | Anion source type | mmol | Temp. °C. | Rate mol/gat/h | Product(s) | Linearity % |
|---|---|---|---|---|---|---|---|
| XVIII | BCPP | MSA | 0.5 | 118 | 200 | $C_4$-aldehyde | 83 |
| | | $SnCl_2$ | 0.5 | | | | |
| XIX | BCPE | MSA | 0.5 | 120 | 100 | $C_4$-aldehyde | 90 |
| | | $SnCl_2$ | 0.5 | | | | |
| XX | BCPE | TFSA | 0.5 | 102 | 550 | $C_4$-aldehyde | 94 |
| | | $SnCl_2$ | 0.5 | | | | |

EXAMPLES XXI–XXV

The experiments were performed, substantially as described in Examples XIX and XX, using different olefins and substituted olefins, instead of propene.

In all experiments the anion source was 0.5 mmol of TFSA and 0.5 mmol of $SnCl_2$.

Further details and results are provided in Table V.

TABLE V

| Ex. No. | Reactant mL | Ligand | Temp °C. | Rate mol/gat/h | Product(s) Selectivity % | Linearity |
|---|---|---|---|---|---|---|
| XXI | ethene | BCPE | 90 | 1500 | $C_3$-aldehyde 98 | |
| XXII | 1,5-hexadiene 10 | BCPE | 92 | 300 | octanedial 98 | 92 |
| XXIII | norbornadiene 10 | BCPE | 92 | 750 | norbornadi-aldehyde 98 | |
| XXIV | allylacetate 10 | BCPE | 75 | 150 | 4-acetyloxy-butanal 98 | 95 |
| XXV | 4-pentenoic acid | BCPE | 80 | 200 | 5-carboxy-pentanal 95 | 95 |

What is claimed is:

1. A process for the hydroformylation of ethylenically unsaturated compounds to produce aldehydes and/or alcohols by reaction of said ethylenically unsaturated compounds with carbon monoxide and hydrogen in the presence of a catalyst system comprising:
   a) a source of a metal of the platinum group;
   b) a source of anions; and
   c) a source of bidentate ligands of the formula $$R^1R^2M^1RM^2R^3R^4 \qquad (I)$$

wherein $M^1$ and $M^2$ independently represent a phosphorus, arsenic or antimony atom, R represents a bivalent organic bridging group containing from 1 to 4 atoms in the bridge, $R^1$ and $R^2$ together represent a bivalent substituted or non-substituted cyclic group wherein the two free valencies are linked to $M^1$, and wherein $R^3$ and $R^4$ either independently represent a substituted or non-substituted hydrocarbyl group, or together have the same meaning as $R^1$ and $R^2$.

2. The process as claimed in claim 1, characterized in that said source of a metal of the platinum group is selected from the group consisting of a palladium compound, a platinum compound and mixtures thereof.

3. The process as claimed in claim 1, characterized in that said source of anions is selected from a source of non-coordinating or weakly coordinating anions.

4. The process as claimed in claim 3, characterized in that said source of anions is a sulfonic acid.

5. The process as claimed in claim 1, characterized in that the catalyst system comprises as source of anions a combination of a Lewis acid and a protic acid.

6. The process as claimed in claim 5, characterized in that, as Lewis acid, a metal halide is used.

7. The process as claimed in claim 6, characterized in that, as Lewis acid, tin (II)-chloride is used.

8. The process as claimed in claim 1, characterized in that in the bidentate ligand of formula (I), $M^1$ and $M^2$ each represent a phosphorus atom.

9. The process as claimed in claim 1, characterized in that in the bidentate ligand of formula (I), R represents an ethylene group.

10. The process as claimed in claim 1, characterized in that in the bidentate ligand of formula (I), the bivalent cyclic group, represented by $R^1$ together with $R^2$ is a cycloalkylene group having from about 6 to about 9 ring atoms.

11. The process as claimed in claim 10, characterized in that the bivalent cyclic group has 8 ring atoms.

12. The process as claimed in claim 11, characterized in that the bivalent cyclic group is a 1,5-cyclooctylene group.

13. The process as claimed in claim 1, characterized in that $R^3$ together with $R^4$ has the same meaning as $R^1$ together with $R^2$ and wherein the two free valencies are linked to $M^2$.

14. The process as claimed in claim 1, characterized in that the bidentate ligand of formula (I) is bis (1,4-cyclooctylene phosphino)ethane.

15. The process as claimed in claim 1, characterized in that the molar amount of bidentate ligand per gram atom of platinum group metal is in the range of about 0.5 to about 10.

16. The process as claimed in claim 1, characterized in that the molar amount of anion source per gram atom of platinum group metal, is in the range of about 0.5 to about 15.

17. The process as claimed in claim 1, characterized in that the amount of catalyst is such that per mole of ethylenically unsaturated compound, about $10^{-7}$ to about $10^{-2}$ gram atom of platinum group metal is present.

18. The process as claimed in claim 1, characterized in that as ethylenically unsaturated compound(s), one or more olefins having from 2 to about 24 carbon atoms per molecule is (are) used.

19. The process as claimed in claim 18, characterized in that as ethylenically unsaturated compound(s), one or more internal olefins having from about 4 to about 20 carbon atoms per molecule is (are) used.

20. The process as claimed in claim 1, characterized in that the molar ratio of carbon monoxide to hydrogen is in the range of from about 3:1 to about 1:3.

21. The process as claimed in claim 1, characterized in that the hydroformylation is carried out at a temperature in the range of from about 50° C. to about 160° C.

22. The process as claimed in claim 1, characterized in that the hydroformylation is carried out a pressure in the range of from about 5 bar to about 100 bar.

23. The process as claimed in claim 1, characterized in that the hydroformylation is carried out in the presence of a solvent.

24. The process as claimed in claim 23, characterized in that said solvent is an alcohol having from about 4 to about 10 carbon atoms.

* * * * *